US010716707B2

(12) United States Patent
Hess et al.

(10) Patent No.: US 10,716,707 B2
(45) Date of Patent: Jul. 21, 2020

(54) VISION STRENGTHENING METHODS AND SYSTEMS

(71) Applicant: THE ROYAL INSTITUTION FOR THE ADVANCEMENT OF LEARNING / MCGILL UNIVERSITY, Montreal (CA)

(72) Inventors: Robert F. Hess, Montreal (CA); Reza Farivar-Mohseni, Montreal (CA); Alexandre Reynaud, Montreal (CA)

(73) Assignee: THE ROYAL INSTITUTION FOR THE ADVANCEMENT OF LEARNING/MCGILL UNIVERSITY, Montreal, QC (CA)

(*) Notice: Subject to any disclaimer, the term of this patent is extended or adjusted under 35 U.S.C. 154(b) by 359 days.

(21) Appl. No.: 15/507,041

(22) PCT Filed: Aug. 27, 2015

(86) PCT No.: PCT/CA2015/000479
§ 371 (c)(1),
(2) Date: Feb. 27, 2017

(87) PCT Pub. No.: WO2016/029295
PCT Pub. Date: Mar. 3, 2016

(65) Prior Publication Data
US 2017/0281412 A1 Oct. 5, 2017

Related U.S. Application Data

(60) Provisional application No. 62/042,293, filed on Aug. 27, 2014.

(51) Int. Cl.
A61F 9/008 (2006.01)
A61B 3/08 (2006.01)
(Continued)

(52) U.S. Cl.
CPC ............ *A61F 9/00829* (2013.01); *A61B 3/08* (2013.01); *A61F 9/022* (2013.01); *A61H 5/00* (2013.01);
(Continued)

(58) Field of Classification Search
CPC .............................. A61F 9/0029; A61B 3/08
See application file for complete search history.

(56) References Cited

U.S. PATENT DOCUMENTS 8,057,036 B2 † 11/2011 Hess
8,066,372 B2 † 11/2011 Cooperstock
(Continued)

OTHER PUBLICATIONS

To, L. et al.: "A Game Platform for Treatment of Amblyopia", IEEE Transactions on Neural Systems and Rehabilitationengineering., Jun. 2011, vol. 19, No. 3, pp. 280-289.
(Continued)

Primary Examiner — Girumsew Wendmagegn
(74) Attorney, Agent, or Firm — Anglehart et al.

(57) ABSTRACT

Active dichoptic perceptual-learning tasks or dichoptic game play have been shown to significantly improve visual acuity of amblyopic children and adults. However, these dichoptic perceptual learning tasks are intensive and repetitive such that non-compliance is high. In contrast, the invention provides dichoptic perceptual learning in a manner that the user maintains its use and compliance is increased. Further, compliance becomes automatic if the user performs tasks in a normal manner and "forgets" that they are actually undergoing treatment as it is integrated with minimal disruption to their life and activities. Accordingly, a methodology exploiting complementary dichoptic stimulation is presented.

18 Claims, 8 Drawing Sheets

(51) Int. Cl.
*A61H 5/00* (2006.01)
*A61F 9/02* (2006.01)

(52) U.S. Cl.
CPC ..... *A61F 9/008* (2013.01); *A61F 2009/00846* (2013.01); *A61H 2201/165* (2013.01); *A61H 2201/5007* (2013.01); *A61H 2201/5043* (2013.01); *A61H 2201/5097* (2013.01)

(56) References Cited

U.S. PATENT DOCUMENTS

| | | | |
|---|---|---|---|
| 8,454,166 B2 † | 6/2013 | Fateh | |
| 9,370,460 B2 † | 6/2016 | Vadai | |
| 9,706,910 B1 † | 7/2017 | Blaha | |
| 2006/0087618 A1* | 4/2006 | Smart | A61B 3/005 351/222 |
| 2010/0073469 A1* | 3/2010 | Fateh | A61H 5/00 348/62 |
| 2010/0201942 A1* | 8/2010 | Hess | A61B 3/022 351/201 |
| 2012/0069296 A1 | 3/2012 | Li et al. | |
| 2012/0179076 A1 | 7/2012 | Bavelier et al. | |

OTHER PUBLICATIONS

Choubey, B. et al. ; "Methods for Dichoptic Stimulus Presentation in Functional Magnetic Resonance Imaging.", The Open Neuroimaging Journal, 2009, vol. 3, pp. 17-25.
European Search Report of Application No. 15837049.4, dated Mar. 23, 2018.
To, L., Thompson, J. A Game Platform for Treatment of Amblyopia, IEEE Transactions on Neural Systems and Rehabilitation Engineering. vol. 19, No. 3, Jun. 2011, pp. 280-289.
Choubey, B., Jurcoane, A. Method for Dichoptic Stimulus Presentation in Functional Magnetic Resonance Imaging. The Open Neuroimaging Journal, 2009, 3, pp. 17-25.
International Search Report dated Oct. 29, 2015 issued in connection with WO2016/029295.

\* cited by examiner
† cited by third party

VISION STRENGTHENING METHODS AND SYSTEMS

CROSS-REFERENCE TO RELATED APPLICATIONS

The present patent application is a US National Stacie of International Application No. PCT/CA2015/000479, filed on Aug. 27, 2015, which claims the benefit of U.S. Provisional Patent Application 62/042,293 filed Aug. 27, 2014 entitled "A method and system for binocular therapy through unobtrusive complimentary independent dichotic stimulation", the entire contents of which are included by reference.

FIELD OF THE INVENTION

This invention relates to vision and more particularly to providing methods and systems to reduce the extent of binocular dysfunction and/or improve visual function.

BACKGROUND OF THE INVENTION

The human visual processing involves complex actions and interactions of the eyes and the brain. To simplify this description, we can think of the visual system as being composed of three areas of function, namely, acuity, perception, and eye movement. Any one of these functions can be impaired without impairment to the remaining two functions or combinations of impairments may arise from a variety of factors including genetics, disease, and health issues such as heart attacks through to mild traumatic brain injuries.

Visual acuity, commonly refers to the clarity of vision and is similarly dependent upon a combination of optical and neural factors, as is the visual system overall, including for example, the sharpness of the retinal focus within the eye, the health and functioning of the retina, and the sensitivity of the interpretative faculty of the brain. A common cause of low visual acuity is refractive error (ametropia) which can arise from a variety of factors leading to conditions such as pseudomyopia, myopia, and hyperopia whilst optical causes may include astigmatism or more complex corneal irregularities. Typically, such issues are addressed by optical means such as eyeglasses, contact lenses, laser surgery, etc.

Neural factors that limit acuity are located in the retina, the brain, or the pathway connecting them, the optical nerve. Examples for the first are a detached retina and macular degeneration, to name just two, whilst in other cases, low visual acuity is caused by brain damage, such as from traumatic brain injury or stroke. A common impairment is amblyopia resulting from incorrect nerve pathway function connecting the eye with the brain which results in decreased vision in an eye that otherwise appears normal or the decrease is out of proportion to any associated structural problems of the eye. Amblyopia has been classically treated by patching the fellow eye to force use of the amblyopic eye. However, many individuals, especially those who only have a mild form, are not even aware they have the condition until tested at older ages, since the vision in their stronger eye is normal. Individuals with severe amblyopia, however, may experience related visual disorders, including poor depth perception, poor visual acuity, poor spatial acuity, low sensitivity to contrast and motion. Amblyopia is characterized by several functional abnormalities in spatial vision, including reductions in visual acuity (VA), contrast sensitivity function (CSF), and Vernier acuity as well as spatial distortion, abnormal spatial interactions, and impaired contour detection. In addition, individuals with amblyopia suffer from binocular abnormalities such as impaired stereoacuity (stereoscopic acuity) and abnormal binocular summation.

Within the prior art there is an increasing understanding of the role of binocular dysfunction (suppression) in amblyopia that has motivated a reformulation of amblyopia treatment. Many amblyopic patients have a structurally intact binocular visual system that can be revealed by decreasing the fellow-eye contrast to reduce interocular suppression. Accordingly, repeated active dichoptic perceptual-learning tasks or dichoptic game play have been shown to significantly improve visual acuity of amblyopic children and adults. Such dichoptic tasks and games provide contrast-balanced binocular vision, with low contrast for the fellow eye and high contrast for the amblyopic eye. However, these dichoptic perceptual learning tasks are intensive and repetitive and the dichoptic games used to date have limited appeal resulting in approximately 40% of unsupervised patients becoming non-compliant with even only 16 hours of assigned activity over a 4 week period.

Accordingly, it would be beneficial to provide a method or system that provides the required dichoptic perceptual learning but in a manner that the user maintains its use and compliance is increased. It would be further beneficial to provide this method or system in a manner that the user performs tasks in a normal manner and "forgets" that they are actually undergoing treatment as it is integrated with minimal disruption to their lift and activities. Accordingly, the inventors have established a methodology exploiting complementary dichoptic stimulation for addressing binocular amblyopia within normal environments through their use of display devices in their everyday activities.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to mitigate limitations in the prior art relating to vision and more particularly to providing methods and systems to reduce the extent of binocular dysfunction and/or improve visual function.

In accordance with an embodiment of the invention there is provided a method comprising establishing a first image for presentation to a left eye of a user and a second image for presentation to a right eye of the user, each of the first image and the second image generated by modification of a source image in dependence upon a characteristic of at least one of a neural condition and a neurological condition of the user, wherein neither the user's left eye or right eye receive a complete representation of the source image.

In accordance with an embodiment of the invention there is provided a system comprising a module, the module comprising:
 a first port for receiving first electronic content for display to a user;
 a second port for providing second electronic content to a display device associated with the user; and
 a processing circuit for modifying the first electronic content to generate the second electronic content; wherein the modification is such that a left eye of a user and a right eye of the user receive different images and such that the modified content for either the user's left eye or right eye is also modified according to a characteristic of a neurological condition of the user and neither the user's left eye or right eye receive a complete representation of the electronic content.

Executable instructions for execution by a processor stored upon a non-volatile, non-transitory storage medium which when executed result in a process being performed, the process comprising establishing a first image for presentation to a left eye of a user and a second image for presentation to a right eye of the user, each of the first image and the second image generated by modification of a source image in dependence upon a characteristic of an optical condition of the user, wherein neither the user's left eye or right eye receive a complete representation of the source image.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
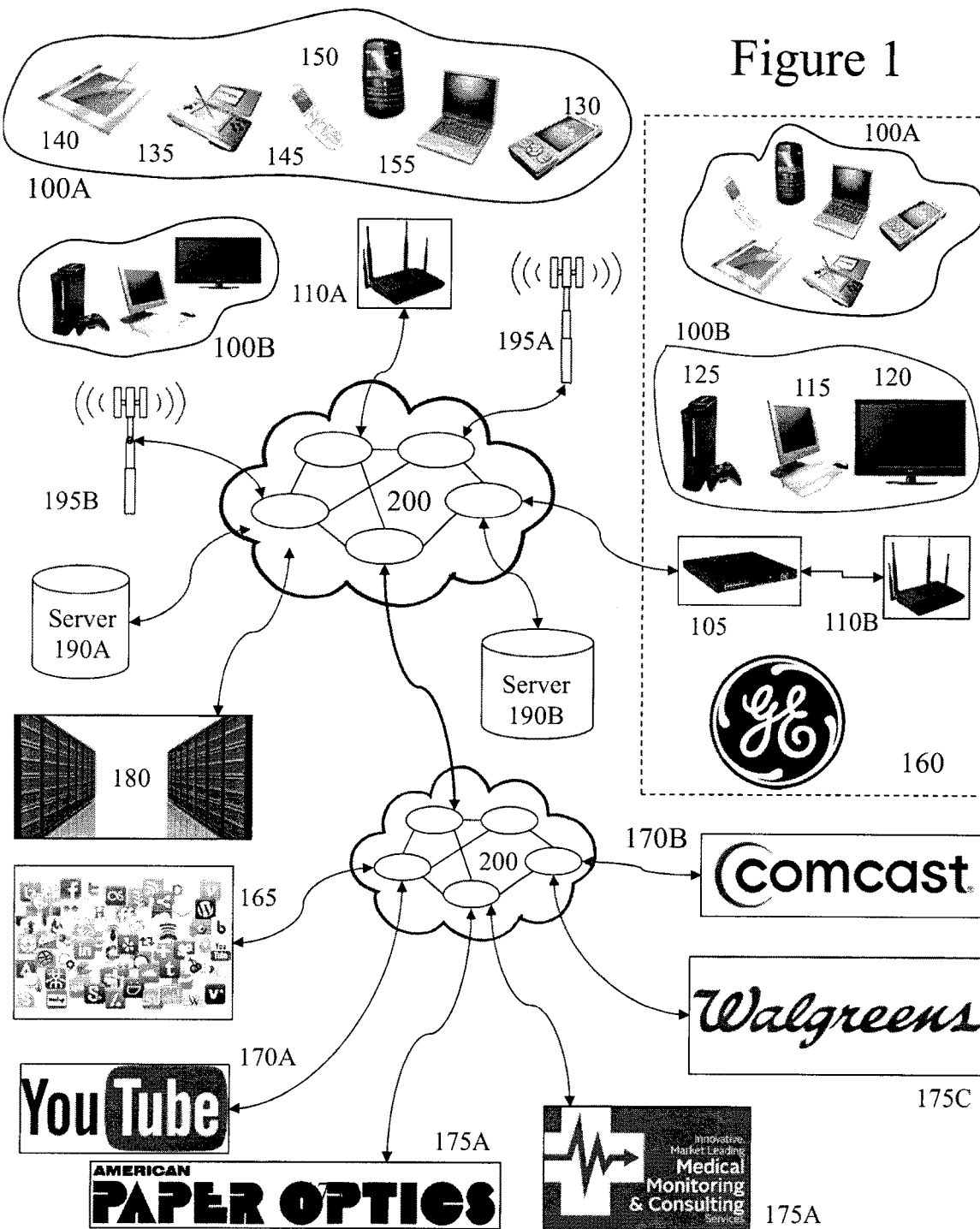
FIG. 1 depicts a network environment within which embodiments of the invention may be employed.

The present invention is directed to vision and more particularly to providing methods and systems to reduce the extent of binocular dysfunction and/or improve visual function.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

A "portable electronic device" (PED) as used herein and throughout this disclosure, refers to a wireless device used for communications and other applications that requires a battery or other independent form of energy for power. This includes devices, but is not limited to, such as a cellular telephone, smartphone, personal digital assistant (PDA), portable computer, pager, portable multimedia player, portable gaming console, laptop computer, tablet computer, and an electronic reader.

A "fixed electronic device" (FED) as used herein and throughout this disclosure, refers to a wireless and/or wired device used for communications and other applications that requires connection to a fixed interface to obtain power. This includes, but is not limited to, a laptop computer, a personal computer, a computer server, a kiosk, a gaming console, a digital set-top box, an analog set-top box, an Internet enabled appliance, an Internet enabled television, and a multimedia player.

An "application" (commonly referred to as an "app") as used herein may refer to, but is not limited to, a "software application" and an element of a "software suite" as used herein may refer to, but is not limited to, a computer program designed to allow an individual to perform an activity. An application thus differs from an operating system (which runs a computer), a utility (which performs maintenance or general-purpose chores), and a programming tools (with which computer programs are created). Generally, within the following description with respect to embodiments of the invention an application is generally presented in respect of software permanently and/or temporarily installed upon a PED and/or FED for the purposes of presenting a micro-survey to a consumer and/or customer.

A "social network" or "social networking service" as used herein may refer to, but is not limited to, a platform to build social networks or social relations among people who may, for example, share interests, activities, backgrounds, or real-life connections. This includes, but is not limited to, social networks such as U.S. based services such as Facebook, Google+, Tumblr and Twitter; as well as Nexopia, Badoo, Bebo, VKontakte, Delphi, Hi5, Hyves, iWiW, Nasza-Klasa, Soup, Glocals, Skyrock, The Sphere, StudiVZ, Tagged, Tuenti, XING, Orkut, Mxit, Cyworld, Mixi, renren, weibo and Wretch.

"Social media" or "social media services" as used herein may refer to, but is not limited to, a means of interaction among people in which they create, share, and/or exchange information and ideas in virtual communities and networks. This includes, but is not limited to, social media services relating to magazines, Internet forums, weblogs, social blogs, microblogging, wikis, social networks, podcasts, photographs or pictures, video, rating and social bookmarking as well as those exploiting blogging, picture-sharing, video logs, wall-posting, music-sharing, crowdsourcing and voice over IP, to name a few. Social media services may be classified, for example, as collaborative projects (for example, Wikipedia); blogs and microblogs (for example, Twitter™); content communities (for example, YouTube and DailyMotion); social networking sites (for example, Facebook™); virtual game-worlds (e.g., World of Warcraft™); and virtual social worlds (e.g. Second Life™).

An "enterprise" as used herein may refer to, but is not limited to, a provider of a service and/or a product to a user, customer, or consumer. This includes, but is not limited to, a retail outlet, a store, a market, an online marketplace, a manufacturer, an online retailer, a charity, a utility, and a service provider. Such enterprises may be directly owned and controlled by a company or may be owned and operated by a franchisee under the direction and management of a franchiser.

A "service provider" as used herein may refer to, but is not limited to, a third party provider of a service and/or a product to an enterprise. This includes, but is not limited to, a retail outlet, a store, a market, an online marketplace, a manufacturer, an online retailer, a utility, an own brand provider, and a service provider wherein the service and/or product is at least one of marketed, sold, offered, and distributed by the enterprise solely or in addition to the service provider.

A 'third party' or "third party provider" as used herein may refer to, but is not limited to, a so-called "arm's length" provider of a service and/or a product to an enterprise and/or service provider wherein the consumer and/or customer engages the third party but the actual service and/or product that they are interested in and/or purchase.

A "user" as used herein may refer to, but is not limited to, an enterprise, a service provider, and an individual accessing at least one of publishing software and/or publishing software according to embodiments of the invention from the viewpoint of publishing information.

"User information" as used herein may refer to, but is not limited to, user behavior information and/or user profile information. It may also include a user's biometric information, an estimation of the user's biometric information, or a projection/prediction of a user's biometric information derived from current and/or historical biometric information.

A "wearable device" or "wearable sensor" relates to miniature electronic devices that are worn by the user including those under, within, with or on top of clothing and are part of a broader general class of wearable technology which includes "wearable computers" which in contrast are directed to general or special purpose information technologies and media development. Such wearable devices and/or wearable sensors may include, but not be limited to, smartphones, smart watches, e-textiles, smart shirts, activity trackers, smart glasses, environmental sensors, medical sensors, biological sensors, physiological sensors, chemical sensors, ambient environment sensors, position sensors, neurological sensors, drug delivery systems, medical testing and diagnosis devices, and motion sensors.

Reference to a "document" as used herein may refer to, but is not limited to, any machine-readable and machine-storable work product. A document may be a file, a combination of files, one or more files with embedded links to other files, etc. The files may be of any type, such as text, audio, image, video, etc. Parts of a document to be rendered to an end user can be thought of as "content" of the document. A document may include "structured data" containing both content (words, pictures, etc.) and some indication of the meaning of that content (for example, e-mail fields and associated data, HTML tags and associated data, etc.) Advertisement spots in the document may be defined by embedded information or instructions. In the context of the Internet, a common document is a Web page. Web pages often include content and may include embedded information (such as meta information, hyperlinks, etc.) and/or embedded instructions (such as Javascript, etc.). In many cases, a document has a unique, addressable, storage location and can therefore be uniquely identified by this addressable location such as a universal resource locator (URL) for example used as a unique address used to access information on the Internet.

A "mask" as used herein may refer to, but is not limited to, a spatial and/or temporal adjustment made to one or more regions of an image being presented to a user. Accordingly, the mask may within embodiments of the invention remove content within the one or more regions of the image or within other embodiments of the invention the one or more regions of the image may be presented as, for example, as a blurred version, a low contrast version, a lower intensity, a higher intensity, spectrally adjusted, and with other content not related to the image. Accordingly, such masks may be considered in more general terms as providing display regions or spatio-temporal filters. Accordingly, such regions may be devoid of optical stimuli or include stimuli. However, irrespective of the modification(s) made a common characteristic to them is that they have graded boundaries such that the modification(s) are introduced/removed over a boundary around a region such that the user does not perceive boundaries between modified and unmodified regions.

Referring to FIG. 1 there is depicted a network environment 200 within which embodiments of the invention may be employed supporting publishing systems and publishing applications/platforms (PSPAPs) according to embodiments of the invention. Such PSPAPs, for example supporting multiple channels and dynamic content. As shown first and second user groups 100A and 100B respectively interface to a telecommunications network 200. Within the representative telecommunication architecture a remote central exchange 180 communicates with the remainder of a telecommunication service providers network via the network 200 which may include for example long-haul OC-48/OC-backbone elements, an OC-48 wide area network (WAN), a Passive Optical Network, and a Wireless Link. The central exchange 180 is connected via the network 200 to local, regional, and international exchanges (not shown for clarity) and therein through network 200 to first and second cellular APs 195A and 195B respectively which provide Wi-Fi cells for first and second user groups 100A and 100B respectively. Also connected to the network 200 are first and second Wi-Fi nodes 110A and 110B, the latter of which being coupled to network 200 via router 105. Second Wi-Fi node 110B is associated with Enterprise 160, e.g. General Electric™, within which other first and second user groups 100A and 100B are present. Second user group 100B may also be connected to the network 200 via wired interfaces including, but not limited to, DSL, Dial-Up, DOCSIS, Ethernet, G.hn, ISDN, MoCA, PON, and Power line communication (PLC) which may or may not be routed through a router such as router 105.

Within the cell associated with first AP 110A the first group of users 100A may employ a variety of PEDs including for example, laptop computer 155, portable gaming console 135, tablet computer 140, smartphone 150, cellular telephone 145 as well as portable multimedia player 130. Within the cell associated with second AP 110B are the second group of users 100B which may employ a variety of FEDs including for example gaming console 125, personal computer 115 and wireless/Internet enabled television 120 as well as cable modem 105. First and second cellular APs 195A and 195B respectively provide, for example, cellular GSM (Global System for Mobile Communications) telephony services as well as 3G and 4G evolved services with enhanced data transport support. Second cellular AP 195B provides coverage in the exemplary embodiment to first and second user groups 100A and 100B. Alternatively the first and second user groups 100A and 100B may be geographically disparate and access the network 200 through multiple APs, not shown for clarity, distributed geographically by the network operator or operators. First cellular AP 195A as show provides coverage to first user group 100A and environment 170, which comprises second user group 100B as well as first user group 100A. Accordingly, the first and second user groups 100A and 100B may according to their particular communications interfaces communicate to the network 200 through one or more wireless communications standards such as, for example, IEEE 802.11, IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, and IMT-2000. It would be evident to one skilled in the art that many portable and fixed electronic devices may support multiple wireless protocols simultaneously, such that for example a user may employ GSM services such as telephony and SMS and Wi-Fi/WiMAX data transmission, VOIP and Internet access. Accordingly portable electronic devices within first user group 100A may form associations either through standards such as IEEE 802.15 and Bluetooth as well in an ad-hoc manner.

Also connected to the network 200 are Social Networks (SOCNETS) 165, first and second content providers 170A and 170B respectively, e.g. YouTube™ and Comcast™, and first to third party providers 175A to 175C respectively, e.g. Medical Monitoring Service, American Paper Optics™ (a three-dimensional glasses supplier), and Walgreen's (a pharmacy company), as well as first and second servers 190A and 190B which together with others, not shown for clarity. First and second servers 190A and 190B may host according to embodiments of the inventions multiple services associated with a provider of publishing systems and publishing applications/platforms (PSPAPs); a provider of a SOCNET or Social Media (SOME) exploiting PSPAP features; a provider of a SOCNET and/or SOME not exploiting PSPAP features; a provider of services to PEDS and/or FEDS; a provider of one or more aspects of wired and/or wireless communications; an Enterprise 160 exploiting PSPAP features; license databases; content databases; image databases; content libraries; customer databases; websites; and software applications for download to or access by FEDs and/or PEDs exploiting and/or hosting PSPAP features. First and second primary content servers 190A and 190B may also host for example other Internet services such as a search engine, financial services, third party applications and other Internet based services.

Accordingly, a consumer and/or customer (CONCUS) may exploit a PED and/or FED within an Enterprise 160, for example, and access one of the first or second primary content servers 190A and 190B respectively to perform an operation such as accessing/downloading an application which provides PSPAP features according to embodiments of the invention; execute an application already installed providing PSPAP features; execute a web based application providing PSPAP features; or access content. Similarly, a CONCUS may undertake such actions or others exploiting embodiments of the invention exploiting a PED or FED within first and second user groups 100A and 100B respectively via one of first and second cellular APs 195A and 195B respectively and first Wi-Fi nodes 110A.

Figure 2:
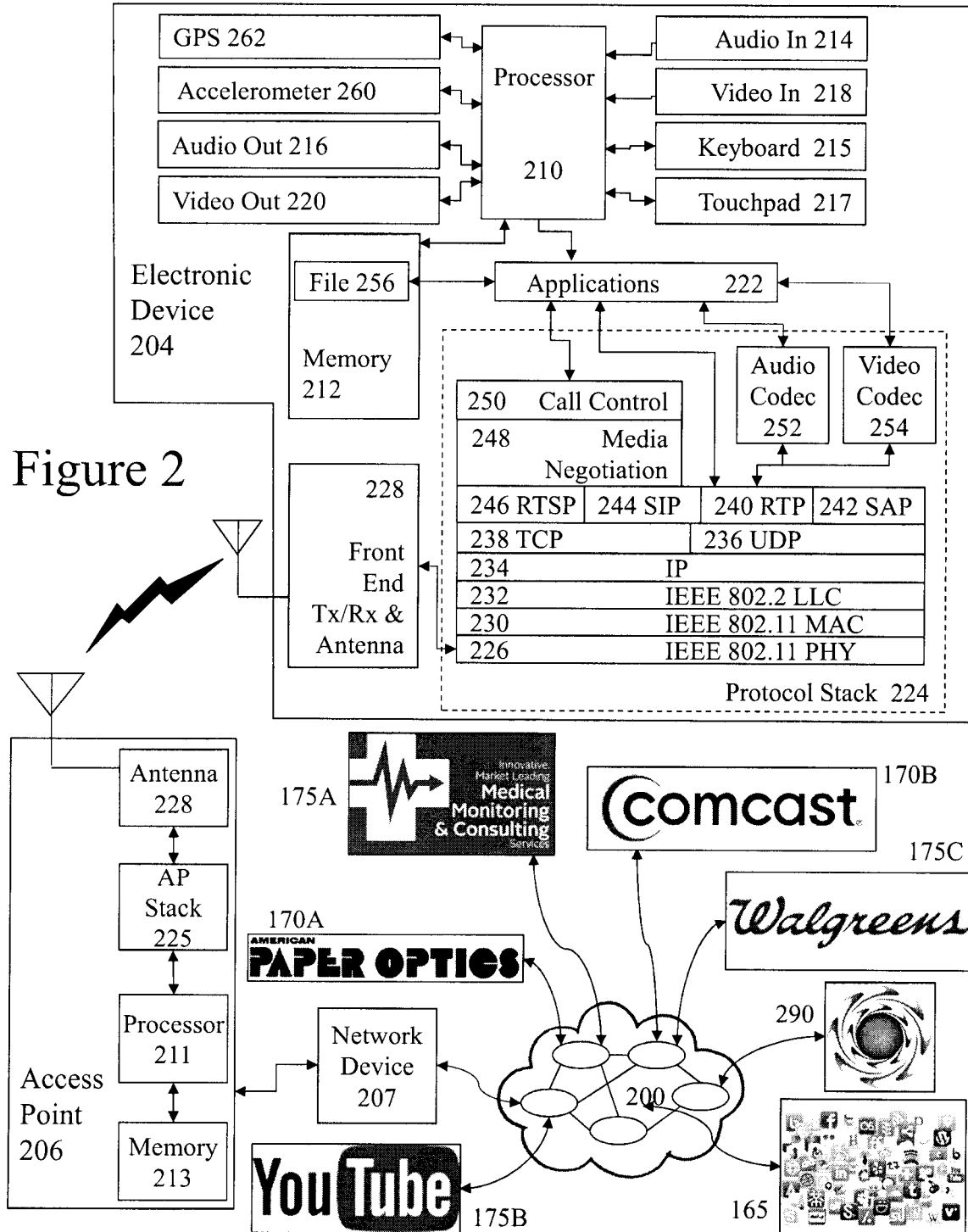
FIG. 2 depicts a wireless portable electronic device supporting communications to a network such as depicted in FIG. 11 and as supporting embodiments of the invention.

Now referring to FIG. 2 there is depicted an electronic device 204 and network access point 207 supporting PSPAP features according to embodiments of the invention. Electronic device 204 may, for example, be a PED and/or FED and may include additional elements above and beyond those described and depicted. Also depicted within the electronic device 204 is the protocol architecture as part of a simplified functional diagram of a system 200 that includes an electronic device 204, such as a smartphone 155, an access point (AP) 206, such as first AP 110, and one or more network devices 207, such as communication servers, streaming media servers, and routers for example such as first and second servers 190A and 190B respectively. Network devices 207 may be coupled to AP 206 via any combination of networks, wired, wireless and/or optical communication links such as discussed above in respect of FIG. 1 as well as directly as indicated. Network devices 207 are coupled to network 200 and therein Social Networks (SOCNETS) 165, first and second content providers 170A and 170B respectively, e.g. YouTube™ and Comcast™, and first to third party providers 175A to 175C respectively, e.g. Medical Monitoring Service, American Paper Optics™ (a three-dimensional glasses supplier), and Walgreen's (a pharmacy company).

The electronic device 204 includes one or more processors 210 and a memory 212 coupled to processor(s) 210. AP 206 also includes one or more processors 211 and a memory 213 coupled to processor(s) 210. A non-exhaustive list of examples for any of processors 210 and 211 includes a central processing unit (CPU), a digital signal processor (DSP), a reduced instruction set computer (RISC), a complex instruction set computer (CISC) and the like. Furthermore, any of processors 210 and 211 may be part of application specific integrated circuits (ASICs) or may be a part of application specific standard products (ASSPs). A non-exhaustive list of examples for memories 212 and 213 includes any combination of the following semiconductor devices such as registers, latches, ROM, EEPROM, flash memory devices, non-volatile random access memory devices (NVRAM), SDRAM, DRAM, double data rate (DDR) memory devices, SRAM, universal serial bus (USB) removable memory, and the like.

Electronic device 204 may include an audio input element 214, for example a microphone, and an audio output element 216, for example, a speaker, coupled to any of processors 210. Electronic device 204 may include a video input element 218, for example, a video camera or camera, and a video output element 220, for example an LCD display, coupled to any of processors 210. Electronic device 204 also includes a keyboard 215 and touchpad 217 which may for example be a physical keyboard and touchpad allowing the user to enter content or select functions within one of more applications 222. Alternatively the keyboard 215 and touchpad 217 may be predetermined regions of a touch sensitive element forming part of the display within the electronic device 204. The one or more applications 222 that are typically stored in memory 212 and are executable by any combination of processors 210. Electronic device 204 also includes accelerometer 260 providing three-dimensional motion input to the process 210 and GPS 262 which provides geographical location information to processor 210.

Electronic device 204 includes a protocol stack 224 and AP 206 includes a communication stack 225. Within system 200 protocol stack 224 is shown as IEEE 802.11 protocol stack but alternatively may exploit other protocol stacks such as an Internet Engineering Task Force (IETF) multimedia protocol stack for example. Likewise AP stack 225 exploits a protocol stack but is not expanded for clarity. Elements of protocol stack 224 and AP stack 225 may be implemented in any combination of software, firmware and/or hardware. Protocol stack 224 includes an IEEE 802.11-compatible PHY module 226 that is coupled to one or more Front-End Tx/Rx & Antenna 228, an IEEE 802.11-compatible MAC module 230 coupled to an IEEE 802.2-compatible LLC module 232. Protocol stack 224 includes a network layer IP module 234, a transport layer User Datagram Protocol (UDP) module 236 and a transport layer Transmission Control Protocol (TCP) module 238.

Protocol stack 224 also includes a session layer Real Time Transport Protocol (RTP) module 240, a Session Announcement Protocol (SAP) module 242, a Session Initiation Protocol (SIP) module 244 and a Real Time Streaming Protocol (RTSP) module 246. Protocol stack 224 includes a presentation layer media negotiation module 248, a call control module 250, one or more audio codecs 252 and one or more video codecs 254. Applications 222 may be able to create maintain and/or terminate communication sessions with any of devices 207 by way of AP 206. Typically, applications 222 may activate any of the SAP, SIP, RTSP, media negotiation and call control modules for that purpose. Typically, information may propagate from the SAP, SIP, RTSP, media negotiation and call control modules to PHY module 226 through TCP module 238, IP module 234, LLC module 232 and MAC module 230.

It would be apparent to one skilled in the art that elements of the electronic device 204 may also be implemented within the AP 206 including but not limited to one or more elements of the protocol stack 224, including for example an IEEE 802.11-compatible PHY module, an IEEE 802.11-compatible MAC module, and an IEEE 802.12-compatible LLC module 232. The AP 206 may additionally include a network layer IP module, a transport layer User Datagram Protocol (UDP) module and a transport layer Transmission Control Protocol (TCP) module as well as a session layer Real Time Transport Protocol (RTP) module, a Session Announcement Protocol (SAP) module, a Session Initiation Protocol (SIP) module and a Real Time Streaming Protocol (RTSP) module, media negotiation module, and a call control module. Portable and fixed electronic devices represented by electronic device 204 may include one or more additional wireless or wired interfaces in addition to the depicted IEEE 802.11 interface which may be selected from the group comprising IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, IMT-2000, DSL, Dial-Up, DOCSIS, Ethernet, G.hn, ISDN, MoCA, PON, and Power line communication (PLC).

A. Inventive Methodology

According to an embodiment of the invention a user suffering a neurological deficit with a visual repercussion, such as amblyopia or traumatic brain injury (TBI) for example, is provided with dichoptic content through performing regular actions and/or dedicated actions exploiting electronic displays such as their television, smart television, three-dimensional television, smartphone, laptop computer, personal computer, etc. Embodiments of the invention may exploit a single display in combination with chromatic filtering or exploit a pair of displays such as present within head mounted displays/virtual reality headsets etc.

According to embodiments of the invention each eye of the user will only see or is only presented an incomplete image of the scene, which may be text, video, multimedia, computer game etc. Accordingly, the segments in both eyes must be pieced together in order to comprehend the full scene. This segmentation of the scene is achieved by applying a patterned image mask to one eye, and a second patterned image mask to the other eye. In some embodiments the second patterned image is generated using the inverse of the same mask used to create the first patterned image. In this manner the user's eyes each see only scattered segments of one image, with the images in the two eyes being complementary to one another.

These masks may be static or dynamic according to embodiments of the invention. These masks may be regularly shaped or irregularly shaped. These masks may either block or otherwise modify the visual information contained within them (e.g., filter, scramble. etc.). However, the masks to prevent the user establishing boundaries within either or both images can employ graded masking or graded edges to block regions such that there are no "sharp" edges arising from the mask(s).

Figures 3A, 3B:
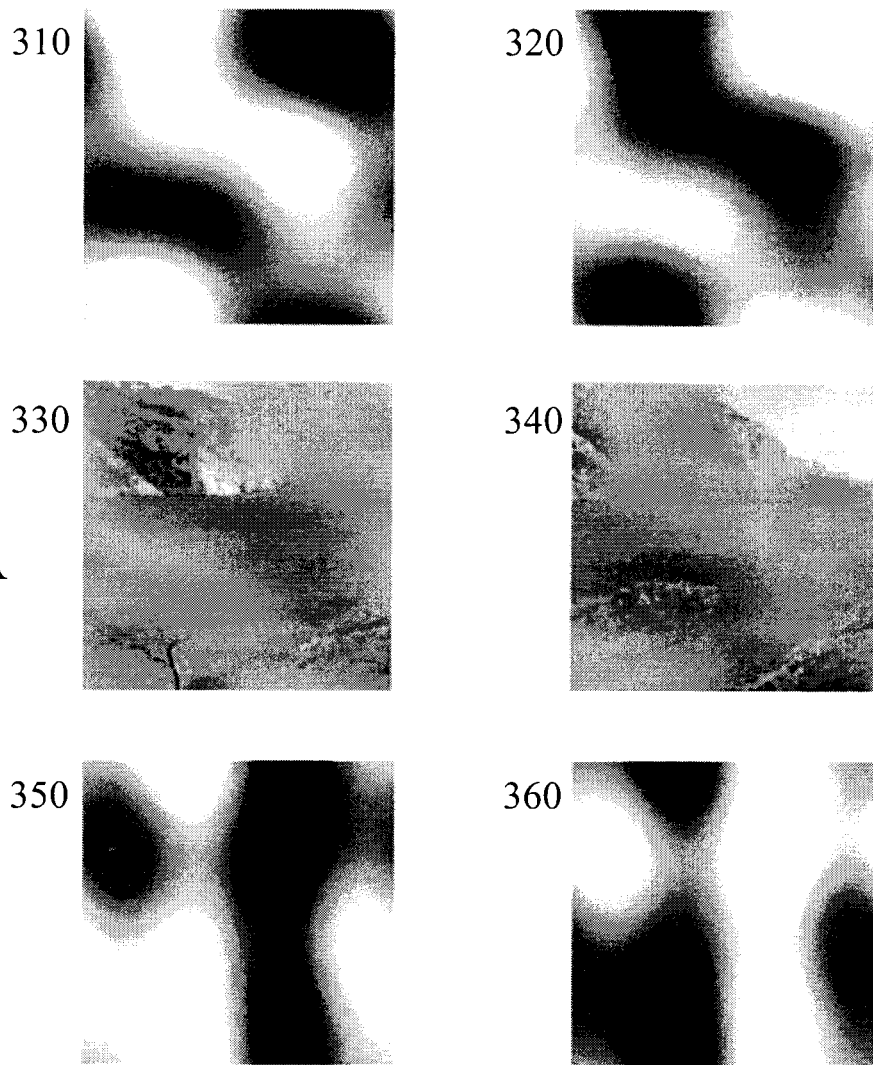
FIG. 3A depicts an image dichoptically segmented for spatial content variation for presentation to a user according to an embodiment of the invention.
FIG. 3B depicts a portion of text dichoptically segmented for spatial content variation for presentation to a user according to an embodiment of the invention.

Referring to FIGS. 3A and 3B there are depicted exemplary images for a user's left and right eyes with their associated masks for image content and text content respectively. Considering FIG. 3A there are depicted first to fourth images 310 to 340 corresponding to:

First image 310 is the mask applied to the content for presentation to the user's left eye;

Second image 320 is the mask applied to the content for presentation to the user's left eye;

Third image 330 representing the image received by the user's left eye;

Fourth image 340 representing the image received by the user's right eye.

Figure 8:
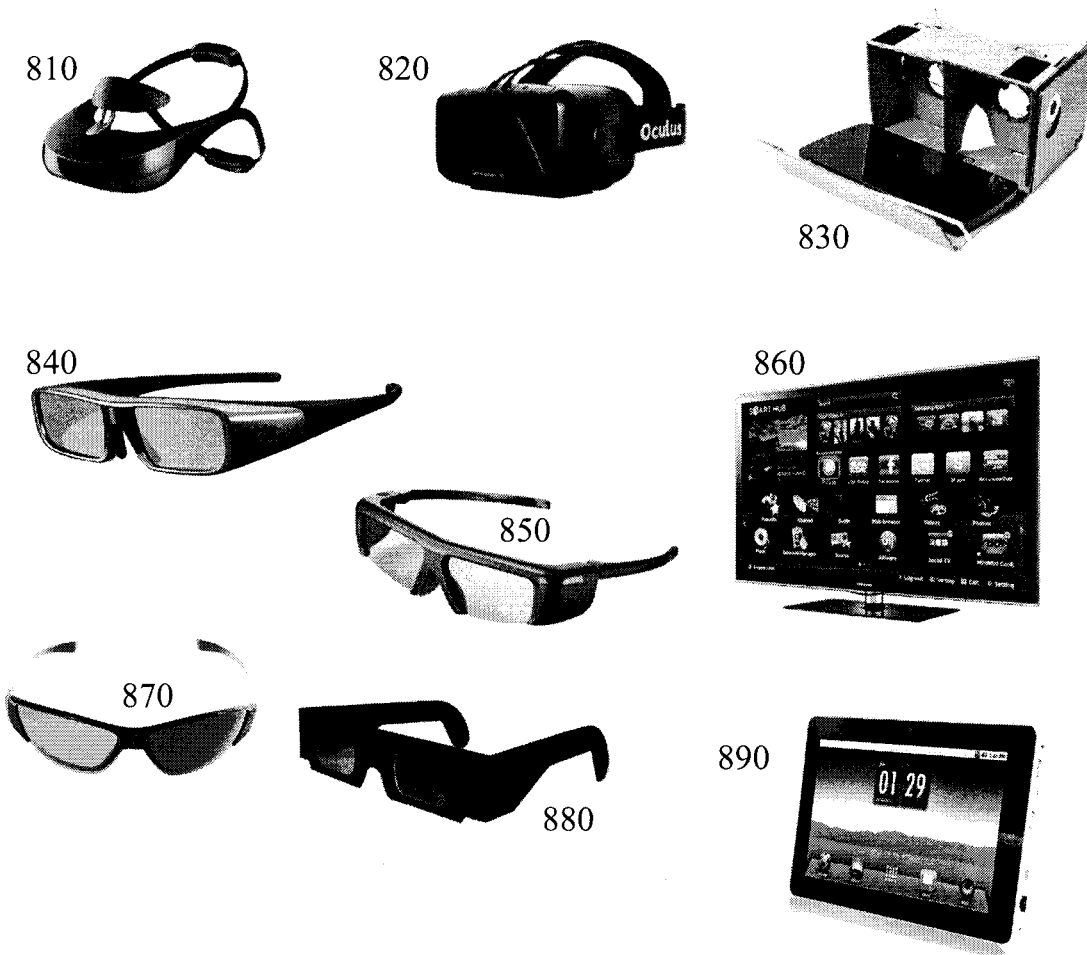
FIG. 8 depicts examples of optical displays, optical glasses, etc. supporting embodiments of the invention.
Figure 8:
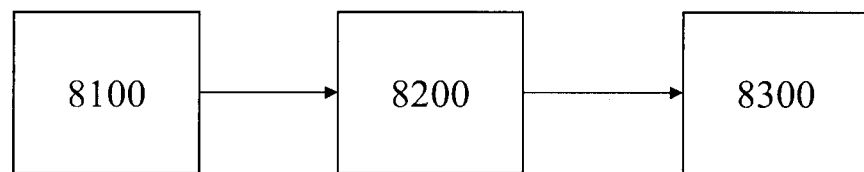

As depicted in FIG. 8 third and fourth images 330 and 340 may be generated as separate images within a dual display environment or as two distinct portions of a single display environment with physical barrier between display and eyes to prevent "cross-over." Alternatively as depicted in FIG. 8 they may be generated with a display and chromatic filtering.

Similarly, referring to FIG. 3B there are depicted first to fourth images 350 to 380 with respect to text, wherein:

First image 350 is the mask applied to the content for presentation to the user's left eye;

Second image 360 is the mask applied to the content for presentation to the user's left eye;

Third image 370 representing the text image received by the user's left eye;

Fourth image 380 representing the text image received by the user's right eye.

Again as depicted in FIG. 8 third and fourth images 370 and 380 may be generated as separate images within a dual display environment or as two distinct portions of a single display environment with physical barrier between display and eyes to prevent "cross-over." Alternatively as depicted in FIG. 8 they may be generated with a display and chromatic filtering.

Accordingly, for patients with amblyopia, the masked images seen by the fellow fixing eye are adjusted so that they do not suppress the image in the amblyopic eye. On the basis of extended treatment over a period of time embodiments of the invention lead to improvements in binocular fusion abilities for these patients. Hence, once a point is reached where the image features are the same in each eye, then there is normal binocular fusion and hence we can then gradually shrink the size of the masking elements so that over time the system reaches the position where both eyes are viewing the same scene without suppression. According to the system implementation users may employ different content including, but not limited to, movies, commercial video games, downloaded electronic books (e-books) etc. In some embodiments of the invention pre-recorded content, e.g. a Hollywood movie, can be pre-processed to allow for the method of dichoptic presentation according to embodiments of the invention. Alternatively, real-time processing of the content may take place on either a computer CPU, a computer's graphical processing unit (GPU) or a dedicated field-programmable gate array (FPGA). Such processors may in some embodiments of the invention be implemented within the display producer, e.g. Blu-Ray™ player or gaming console, through dedicated hardware and/or software and/or firmware. In other embodiments of the invention they are within a dedicated module disposed between, for example, a gaming console, and the display(s) and produce a controllable level of display segmentation and filtering.

The inventors have verified that normal binocular sighted individuals can view content that has modified with complimentary dichoptic random spatial masks and that this can also be done for amblyopes once the image features, most notably the contrast, have been reduced in the fixing eye. The therapeutic outcome arises directly from the methodology as the inventors have shown that over time this procedure strengthens binocular combination and can, in some patients, restore vision. The inventors' novel methodology provides each eye with only an incomplete image of the scene such that the segments in both eyes must be pieced together to comprehend the full scene. The images are purely dichoptic, the segmentation of the scene is achieved by the online dynamic application of complementary patterned image masks dichoptically to each eye.

Figure 4:
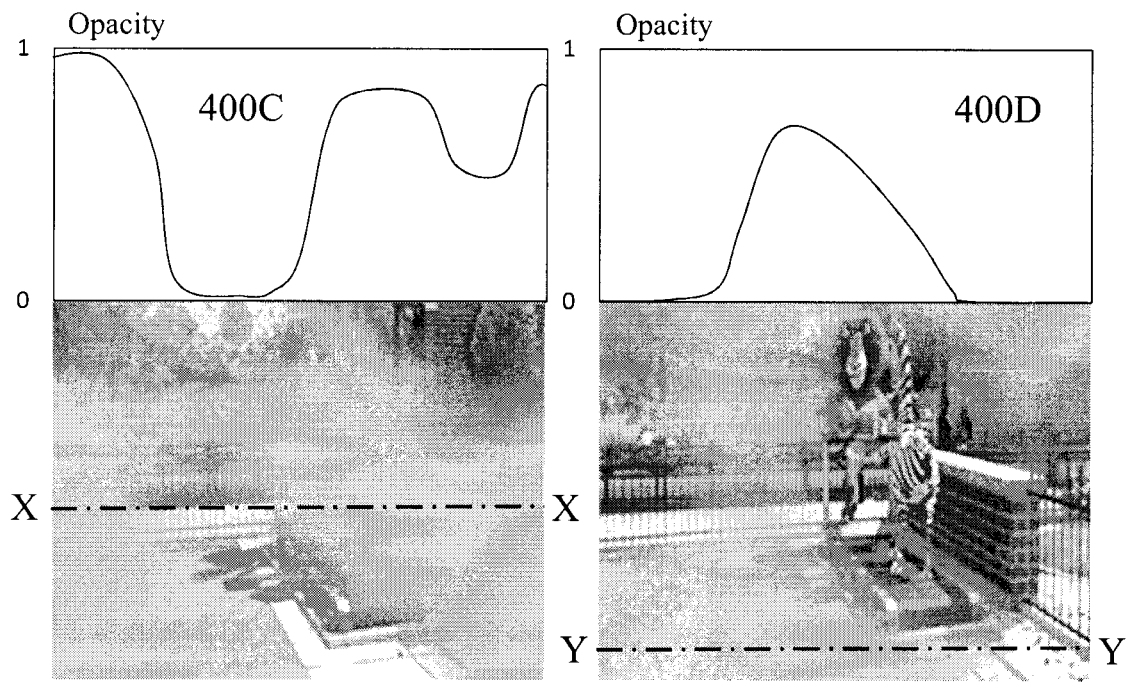
FIG. 4 depicts portions an image dichoptically segmented for spatial content variation for presentation to a user according to an embodiment of the invention together with opacity graphs.

The patterned image masks, as evident from FIGS. 3A to 4, are composed of irregularly shaped blobs produced by low frequency random noise textures. Referring to FIG. 4 first and second opacity graphs 400A and 400B are depicted for sections X-X and Y-Y in first and second images 400C and 400D respectively. As evident the contours are smooth, showing a contrast gradient. On each frame, the mask is multiplied with the image seen by one eye, and the inverse patterned mask is multiplied with the images seen by the other eye. By avoiding sharp profiles the brain's natural processing to define edges and associated objects to shapes is reduced or suppressed.

The masks, also referred to as noise masks, can vary dynamically and their transparency can be manipulated, from totally opaque to invisible. Whilst for ease of visual representation the description in respect of FIGS. 3A to 4 and these embodiments themselves are made with respect to variable intensity, i.e. regions blocked or having high opacity are low intensity, e.g. Opacity=1 that region is dark (no displayed content), it would be evident that other aspects of the images of one eye relative to the other can be varied using this approach to achieve the desired mental processing by the user's brain and over time a therapeutic effect. Optionally, the contrasts of the images seen by each eye can be manipulated independently rather than as complementary of each other. Other dynamic complementary or non-complementary manipulations can be applied to other image parameters such as mean luminance, temporal frequency, spatial frequency, depth, motion, orientation, etc. In all of these cases it is then necessary to piece the two eyes' views together in order to appreciate the content being viewed. Extension to any image parameter is also possible for providing the manipulated content.

B. Clinical Study

B.1 Materials and Methods

B.1.1 Participants

Written informed consent was obtained from all participants/parents. Eight amblyopic children (4-10 years) were referred by two pediatric ophthalmologists. Eligible children had ≥0.5 log minimum angle of resolution (log MAR) amblyopic eye best-corrected visual acuity (BCVA), ≥0.2 log MAR fellow-eye best-corrected visual acuity (BCVA), and ≥0.2 log MAR interocular difference. Strabismic children were only eligible to participate if misalignment of the visual axes had been successfully treated with glasses and/or surgery (defined as ≤0.5pd residual strabismus). In addition, to be eligible, children had to have been wearing spectacle correction for at least 3 months prior to the baseline visit and their referring ophthalmologist had to be willing to forgo other amblyopia treatments during the 2-week study period. Exclusion criteria were prematurity ≥8 weeks, developmental delay, and coexisting ocular or systemic diseases. Medical records were obtained from the referring ophthalmologists to extract diagnosis, cycloplegic refraction, and treatment plan (if any).

B.1.2 Dichoptic Content

During the 2-week study period, children wore glasses with polarized lenses to watch 6 dichoptic movies shown on a passive 3D display in the inventors' laboratory. Dichoptic versions of 18 popular animated feature films were created. A screenshot from one of the movies is shown in FIG. 4 with first and second images 400A and 400B. The high-contrast image, first image 400A, was presented to the amblyopic eye and low-contrast image, second image 400B, to the fellow eye. A patterned image mask composed of irregularly shaped blobs was multiplied with the images seen by the amblyopic eye, and the inverse patterned mask was multiplied with the images seen by the fellow eye. As a result, some parts of the image were only seen by one eye, some parts were only seen by the other eye, and some parts were seen by both eyes. It was necessary to piece the two eyes' views together in order to appreciate the movies. The shape and location of the blobs were varied dynamically every 10 seconds.

B.1.3 Study Protocol

The fellow-eye contrast was initially set individually for each amblyopic child at a reduced level that allowed binocular vision, based on the child's dichoptic motion coherence threshold. Specifically, the initial fellow-eye contrast was set to the dichoptic motion coherence threshold minus 0.10, with a minimum setting of 0.20 and a maximum setting of 0.60. The children traveled to the inventors' laboratory 3 days per week and watched one movie per day. The fellow-eye contrast was incremented by 10% for each subsequent movie (e.g., with an initial fellow-eye contrast setting of 0.30, subsequent movies would have fellow-eye contrasts of 0.33, 0.36, 0.40, 0.44, and 0.48). Each child was accompanied by at least one parent/guardian during the movie sessions to ensure compliance (polarized glasses wear & attention to the movie). Their compliance was also checked by study personnel at 15-30 min intervals.

At the baseline and 2-week outcome visits, BCVA, random dot stereoacuity, and interocular suppression were measured.

Visual Acuity:

BCVA was obtained for each eye with the Amblyopia Treatment Study (ATS) HOTV (ATS-HOTV) (≤7 years) or electronic Early Treatment Diabetic Retinopathy Study (E-ETDRS) (≥7 years) methods.

Stereoacuity:

Random dot stereoacuity was evaluated using the Randot® Preschool Stereoacuity Test, the Stereo Butterfly Test, and Lang-Stereotest I.

Interocular Suppression:

Severity of interocular suppression was quantified using a dichoptic motion coherence test based. Children wore glasses with polarized lenses to view dichoptic random dot kinematograms presented in a 22°-diameter aperture on a passive 3D display. The amblyopic eye saw dots moving in a coherent direction (signal) and the fellow eye saw dots moving in random directions (noise). The task was to indicate the direction of coherent motion. Amblyopic-eye contrast was fixed at 1.0. Fellow-eye contrast was initially set to 0.0 and incremented in a 2-down-1-up staircase to determine the maximum tolerated fellow-eye contrast before the amblyopic eye was suppressed and the child could no longer report the direction of coherent motion. The maximum tolerated fellow-eye contrast provided a quantitative measurement of the severity of suppression; the higher the level, the lower the severity of suppression.

Questionnaire:

In order to informally assess the effect of standard movie and television watching on BCVA on amblyopia, the inventors administered a questionnaire to the parents of the participants. The questionnaire collected retrospective data on how many hours the children watched movies or television shows per day at home prior to the baseline visit, with or without patching. The inventors identified the two consecutive visits to each participant's pediatric ophthalmologist that occurred prior to baseline and extracted the BCVA from the medical records from the two visits to assess the effects of television/movie viewing in visual acuity.

Data Analysis:

Efficacy of watching the dichoptic movies was evaluated using paired t-tests for the primary amblyopic-eye BCVA outcome, and the secondary suppression outcome.

B.2 Results

Eight amblyopic children (4-10 years) were enrolled. Baseline characteristics are summarized in Tables 1A and 1B. The cohort included three children with anisometropic amblyopia, one with strabismic amblyopia and four with combined mechanism amblyopia. Amblyopic-eye visual acuity ranged from 0.50 to 1.20 log MAR at baseline and all had nil stereoacuity. None of the children in the study had manifest tropia following treatment with glasses and/or surgery. Prior to baseline, all children had worn glasses for ≥9 months with excellent compliance. Two participants had no amblyopia treatment prescribed other than spectacle correction prior to the baseline visit. Six children had patching treatment for ≥8 months prior to baseline; 2 had discontinued patching ≥1 year prior to the baseline visit due to lack of continued visual acuity improvement despite reported good compliance and 4 stopped patching in order to participate in the study (these children also reported good compliance with patching).

TABLE 1A

Amblyopic Child Patient Data

| Pt ID | Sex | Age (y) | Type of Amblyopia | Random Dot Stereoacuity | Tropia | Glasses | Strabismus Surgery | Duration (y) |
|---|---|---|---|---|---|---|---|---|
| 1 | M | 4.9 | A | nil | ortho | Y | N | 0.8 |
| 2 | F | 7.2 | A | nil | ortho | Y | N | 1.4 |
| 3 | F | 9.3 | A | nil | ortho | Y | N | 1.8 |
| 4 | F | 7.3 | S | nil | ortho | Y | N | 4.3 |
| 5 | F | 4.7 | C | nil | ortho | Y | Y | 0.8 |
| 6 | F | 7.3 | C | nil | ortho | Y | Y | 3.9 |
| 7 | M | 8.2 | C | nil | ortho | Y | Y | 4.8 |
| 8 | F | 10.7 | C | nil | ortho | Y | N | 4.4 |
| 75% F | | mean = 7.4 | | | Yes | 100% | 38% Y | mean = 2.8 |
| 25% M | | SD = 2.0 | | | No | 0% | 63% N | SD = 1.7 |

Duration = Duration of Spectacle Wear Prior to Baseline

TABLE 1B

Amblyopic Child Patient Data

| Pt ID | Sex | Age (y) | Amblyopic Eye VA (logMar) | Random Dot Stereoacuity | Cycloplegic Refraction Right Eye | Cycloplegic Refraction Left eye |
|---|---|---|---|---|---|---|
| 1 | M | 4.9 | 0.70 | nil | +6.25 + 1.00 × 110 | +5.00 + 1.00 × 085 |
| 2 | F | 7.2 | 1.20 | nil | +2.75 + 2.25 × 100 | +2.50 + 0.25 × 105 |
| 3 | F | 9.3 | 0.80 | nil | +4.50 + 0.50 × 030 | +2.50 + 0.25 × 120 |
| 4 | F | 7.3 | 0.80 | nil | +2.00 + 0.75 × 180 | +1.50 + 1.00 × 180 |
| 5 | F | 4.7 | 0.50 | nil | +1.75 | +3.50 |
| 6 | F | 7.3 | 0.80 | nil | +3.25 + 0.50 × 085 | +1.00 |
| 7 | M | 8.2 | 0.50 | nil | +3.75 | +5.25 |
| 8 | F | 10.7 | 0.50 | nil | +3.00 | +4.25 |
| 75% F | | mean = 7.4 | mean = 0.72 | | | |
| 25% M | | SD = 2.0 | SD = 0.24 | | | |

Figure 5B:
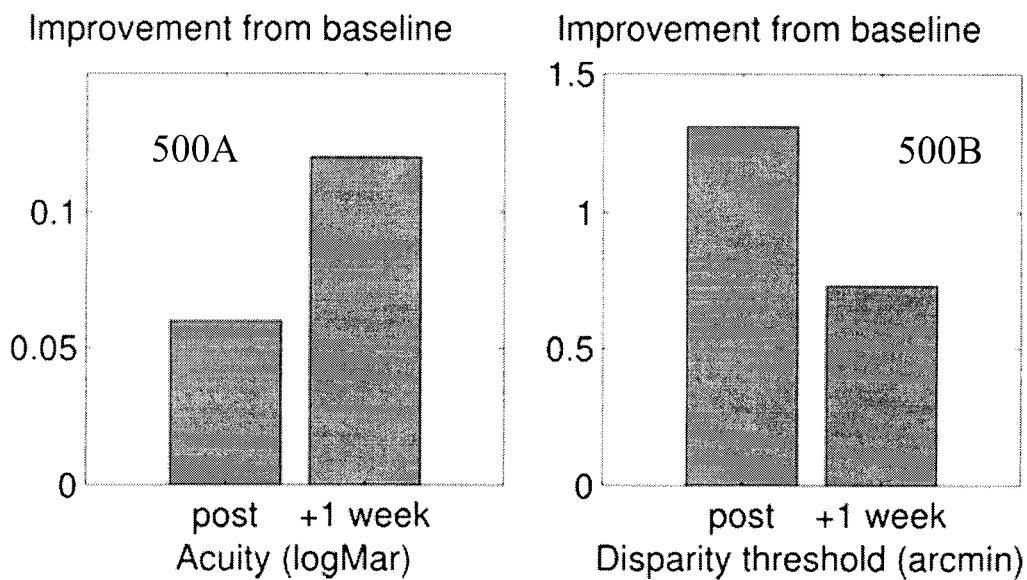
FIG. 5B depicts improvements in visual acuity and stereo acuity for amblyopic subjects employing an embodiment of the invention for one hour daily for two weeks.
Figure 5A:
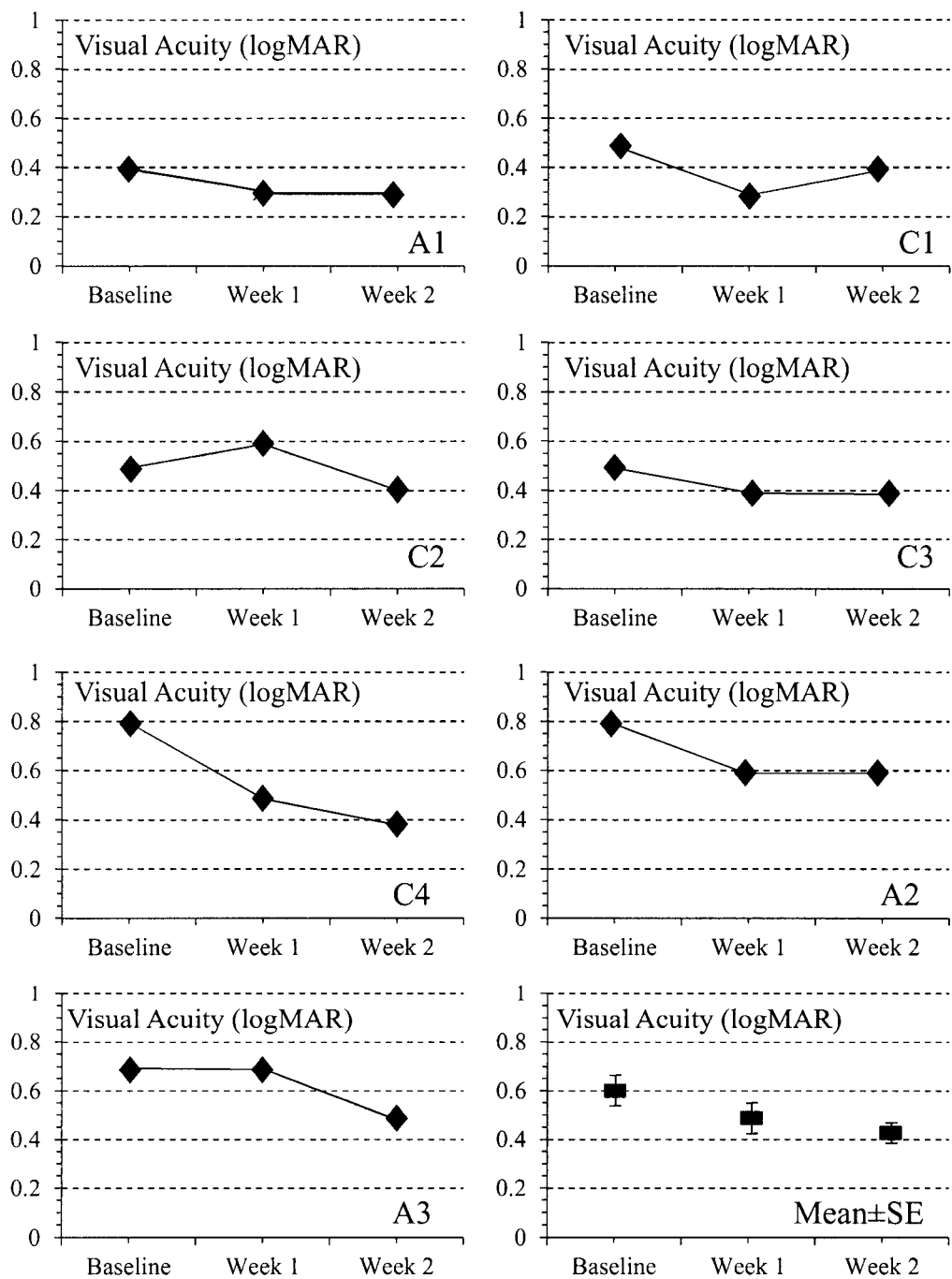
FIG. 5A depicts visual acuity results for eight amblyopic children viewing movies modified according to embodiments of the invention over a two-week period.

During the 2-week study period, each amblyopic child watched 6 dichoptic movies, for a mean (±SD) total time of 9.4±0.9 hours. All children completed the study. Mean (±SD) amblyopic-eye BCVA improved from 0.72±0.08 log MAR at baseline to 0.52±0.09 log MAR at the 2-week visit ($t_7$=4.38; p=0.003; N=8); i.e., 2.0 lines of improvement. As shown in FIG. 5A, all eight children had improved amblyopic-eye BCVA at the 2-Week outcome visit; 3 children with 0.5 log MAR baseline BCVA improved 0.1 log MAR (1 line), 4 children with 0.7-0.8 log MAR baseline BCVA improved 0.2-0.4 log MAR (2-4 lines), and 1 child with 1.2 log MAR baseline BCVA improved 0.1 log MAR (1 line). Fellow-eye BCVA did not change significantly during the 2-week study (mean change±SE=0.04±0.03 log MAR; i.e., 2 letters worse; $t_7$=1.45; p=0.19; N=8).

Interocular suppression was measured in the 7 of the 8 children at baseline and the 2-week outcome visit. In this brief 2-week study, no significant reduction in suppression was found ($t_6$=0.77; p=0.47; N=7).

Parents of 6 out of 8 children responded to the questionnaire about movie and television viewing time prior to the baseline. They all reported that the child watched regularly television 1-2 hours/day during the months prior to the baseline visit. While watching TV or movies, 3 of the children were patching and 3 were not. However, this regular monocular or binocular television viewing at home did not result in a significant improvement in amblyopic eye BCVA. With a mean (±SD) interval of 7.8±3.8 months between the first and second ophthalmology office visits, mean BCVA (±SE) was 0.54±0.11 log MAR on the initial visit and 0.50±0.07 log MAR on the second visit, just before baseline ($t_5$=2.57, p=0.74). In comparison, watching dichoptic movies without concurrent amblyopia treatment resulted in a significant improvement of 2 lines in the amblyopic-eye BCVA after only 2 weeks (about 9.4 hours) of dichoptic stimulation.

B.3 Discussion

In summary, the proof-of-concept study and its results demonstrate that passive viewing of dichoptic feature films provides a methodology for addressing childhood amblyopia. Although a separate control group was not incorporated in the study, our retrospective data showed that regular TV/movie viewing (either monocular or binocular) for months prior to our study did not result in improved amblyopic-eye BCVA. No significant change in the severity of suppression after dichoptic movie watching was found in the current study. During the short proof-of-concept study, children achieved 1-4 lines of visual acuity improvement. This new method improves BCVA rapidly, compared to patching, which has been shown to require 120 hours to achieve one line of improvement in amblyopic children who have already been treated with spectacles for 12-16 weeks.

Within the study the subjects were viewing the movies on a passive 3D screen. To demonstrate platform independence the inventors adapted their masking programs to display the movies dichoptically using a virtual reality headset, Oculus Rift, and obtained the results depicted in FIG. 5B for improvements in visual acuity and stereo acuity on 5 amblyopic subjects who followed a one hour daily training for two weeks. Accordingly, in such a short period with short training sessions the improvements in acuity and disparity threshold were clearly evident. However, it would be evident that the invention may in different implementations be used for extended periods of time per day and extended duration overall as it becomes part of the user's routine viewing.

C. Implementation

Figure 6:
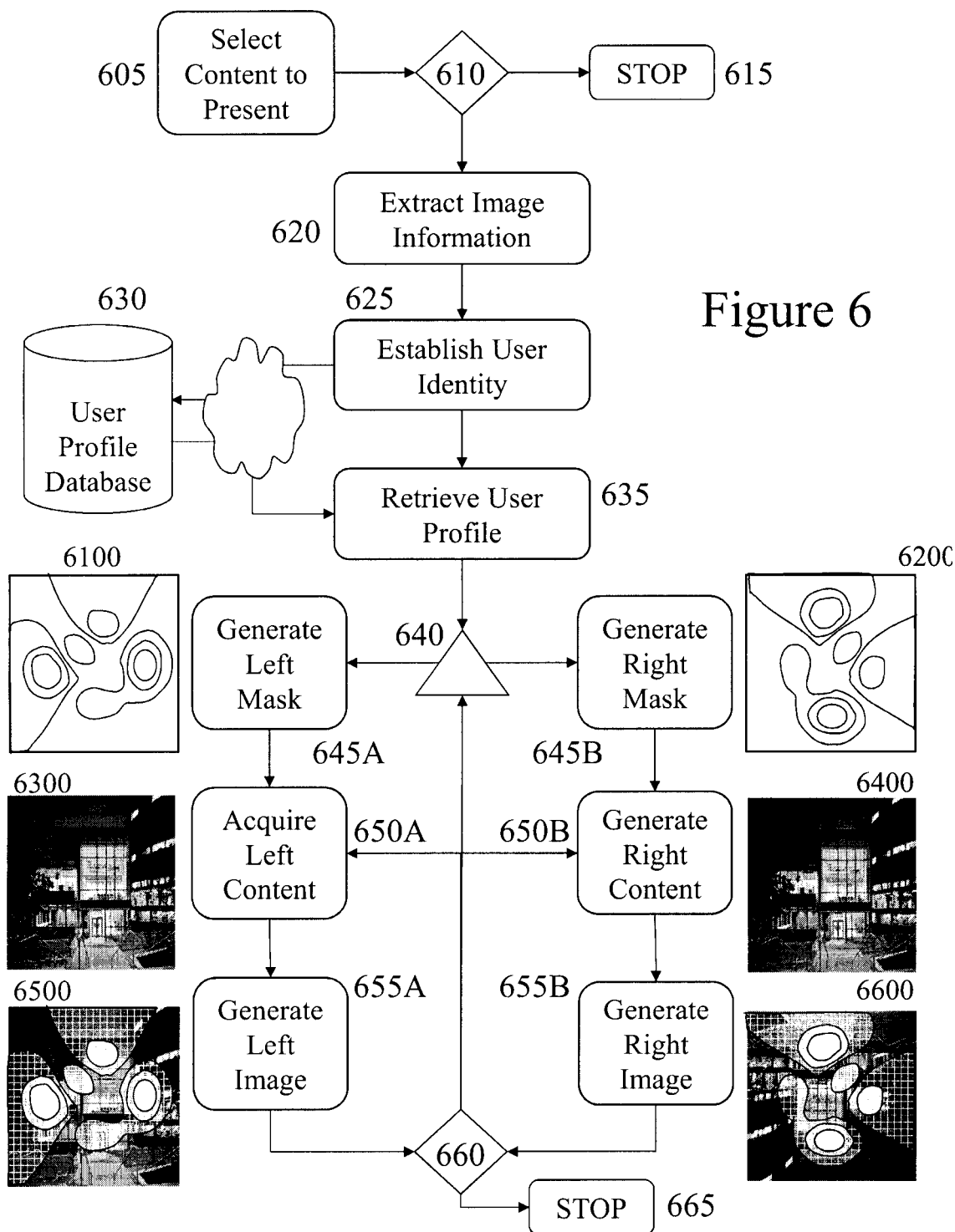
FIG. 6 depicts an exemplary process flow for a system according to an embodiment of the invention exploiting dual display portions with spatial weighting.

Referring to FIG. 6 there is depicted an exemplary process flow for generating an displaying dichoptic content to a user exploiting dual "display" elements, for example a virtual reality headset or barriered single display as depicted and described below in FIG. 8. The process begins at step 605 wherein the user selects content to watch. In step 610 a determination is made with respect to processing as to whether the content will be processed or not, wherein if the content is not going to be processed the process proceeds to step 615 and stops. For example, the image may be spatially uniform, have low contrast, be highly dynamic etc. If the content is to be processed the process proceeds to step 620 and extracts additional image information which is used subsequently for establishing the masks. Next in step 625 the process establishes the user's identity, accesses a user profile data base 630, and in step 635 retrieves a user profile 635 that establishes aspects of the process. Such information may be periodically revised as a user exploits the process and periodically has their eyesight checked. Optionally, a user may periodically be provided with an electronically generated eye test at home wherein a test routine executes with user responses received via keyboard, remote control, voice etc.

Based upon the retrieved user information and extracted image information the process proceeds in steps 645A and 645B respectively to generate the left and right masks 6100/6200 which are then merged with left and right image content 6300/6400 in steps 650A and 650B to form the images to be presented to the user in steps 655A and 655B depicted as images 6500/660. These are then presented and in step 660 the process determines whether new masks are to be generated, wherein the process returns to step 640, whether new content is to be presented, wherein the process returns to steps 650A and 650B or whether the process is complete in which case the process proceeds to step 665 and terminates.

Figure 7:
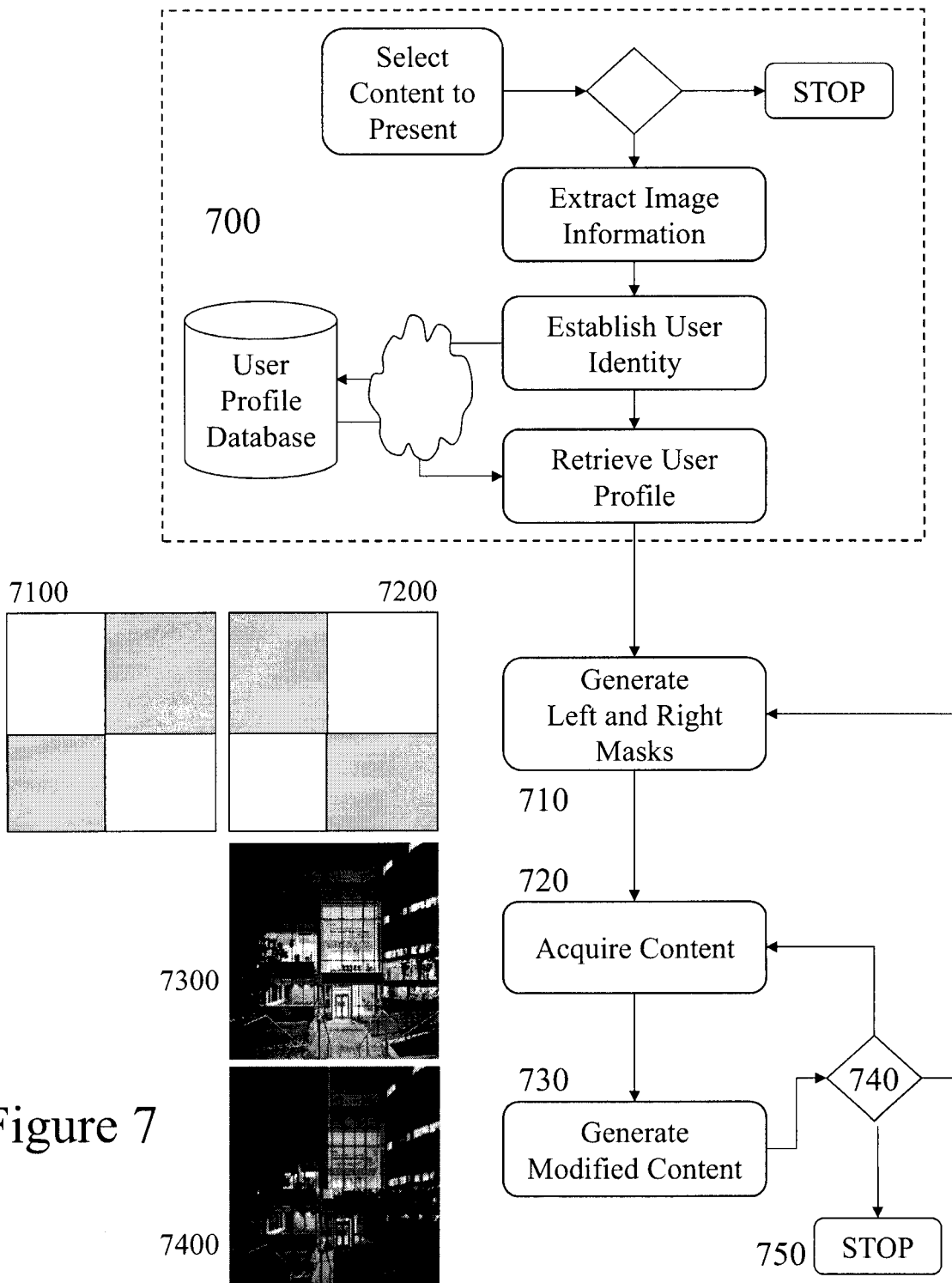
FIG. 7 depicts an exemplary process flow for a system according to an embodiment of the invention exploiting a single display with chromatic weighting.

Now referring to FIG. 7 there is depicted an exemplary process flow for generating an displaying dichoptic content to a user exploiting a single display, for example a television, smartphone, tablet PC, laptop PC, etc. as depicted and described below in FIG. 8. Accordingly, filtering, e.g. chromatic, is established and applied. As depicted the process flow being with sub-flow 700 that incorporates steps 605 to 635 as described and depicted in FIG. 6. From sub-flow 700 the process proceeds to step 710 wherein the left and right masks 7100/7200 are generated, e.g. those being modified in the red/green respectively. For simplicity quadrants are presented but irregular patterns such as those of masks 6100/6200 may be employed with graded shifting. Subsequently, in step 720 the content 7300 is acquired and the modified content 7400 generated in step 730 as presented to the user. Next in step process determines whether new masks are to be generated, wherein the process returns to step 710, whether new content is to be presented, wherein the process returns to step 720 or whether the process is complete in which case the process proceeds to step 750 and terminates.

Referring to FIG. 8 there are depicted examples of displays and ancillary devices supporting embodiments of the invention. First and second images 810 and 820 respectively depict commercial virtual reality headsets from Sony™ 810 and Oculus Rift 820 together with a lost cost do-it-yourself (DIY) cardboard based headset 830. Commercial virtual reality headsets may exploit one display which is partitioned or two displays. As evident in DIY headset 830 a physical barrier separates the images to the left and right eyes from a display or displays providing left and right images. Also depicted are first and second sets of shutter based three-dimensional (3D) glasses 840 and 850 for use with 3D television 860 and first and second sets of chromatic 3D glasses 870 and 890 for use with tablet PC 880 and other display devices. Alternate 3D display technologies include the use of polarizing glasses with orthogonal polarizations for each eye and lenslet technologies that are glasses free, for example. Essentially, the display technologies split into those exploiting discretely provided images to each eye through physical separation and those through optical separation (e.g. polarization, time (shutter), and wavelength).

Referring to flow 8000 content 8100 is processed by a processor 8200 for display upon a device 8300. Within embodiments of the invention processor 8200 may be software upon a tablet PC, laptop PC, smartphone etc. that processes the content 8100 and displays it as a single application. Alternatively, processor 8200 may be a plug-in, application program interface (API) etc. to a content display application such as Windows™ MediaPlayer, Internet Explorer etc. In other embodiments of the invention processor 8200 may be embedded as part of the firmware/software/hardware of the display device 8300 or it may be downloaded to it.

D. Extensions

Whilst the descriptions presented supra in respect of FIGS. 3 to 8 are described and presented in respect of treatment of amblyopia, embodiments of the invention may also address issues for individuals that are insensitive to 3D stereo scenes, or are stereoblind. Up to 30% of the population may be stereoblind, and with increasing availability of 3D TVs and 3D movies, the market for improving depth perception grows accordingly in addition to helping these individuals in their everyday life. This method of dichoptic presentation does not require any perception of depth, but it does require binocular fusion which is also required for stereo-depth perception. Accordingly, the inventors expect improving binocular fusion will also improve stereoscopic depth.

It would be evident that the methods described and presented above may be applied to addressing visual dysfunction in users arising from other diseases including, for example, those that may cause binocular discomfort or scotomas. Examples include traumatic brain injury, heart attack, stroke, demyelinating diseases such as multiple sclerosis (retrobulbar neuritis), damage to nerve fiber layer in the retina due to hypertension or toxic substances, nutritional deficiencies, vascular blockages, and macular degeneration.

It would also be evident that the methods described and presented above may be applied to any disease or condition wherein the cooperative vision of user's pair of eyes is disturbed. It would also be evident it can be applied generally to improving vision even in "normal" individuals as even such "normal individual" represent a distribution of visual functionality and performance wherein these small deviations could be further corrected with the inventive methodologies with an improved vision or specific improvement in binocular function for a subset of the "normal" individuals.

Within the descriptions supra in respect of the specification and the figures images for viewing by a user are modified either prior to their display to the user upon a display forming part of an electronic device or by modifying the view that the user's eye can see, e.g. by programmable optical systems disposed in front of the user's eyes, or by adjusting the view the can see by programmable optical systems. In each instance the modifications made to the image either electronically or optically before the user's retina receives it are made in dependence upon one or more characteristics of their visual dysfunction or visual function. It would be evident that in many instances the user will have their visual acuity tested within a controlled environment such the ophthalmic department of a hospital, medical center, etc. as well in other ophthalmic environments. In these instances parameters relating to the image adjustments/modifications will be generated which require associating with the system(s) the user will employ. In embodiments of the invention this may be made directly at the controlled environment although in other embodiments of the invention the settings may be electronically stored within a server and remotely accessed/downloaded/transferred to the user's system(s) via a network such as the Internet via one or more devices and/or systems such as described supra in respect of FIGS. 1 and 2.

It would also be evident that the user's use of the methodology may be tracked and uploaded for medical review as well as feedback etc. relating to the user's experience via one or more devices and/or systems and/or networks such as described supra in respect of FIGS. 1 and 2. In other embodiments of the invention the settings may be periodically varied based upon user usage, feedback etc. via one or more devices and/or systems and/or networks such as described supra in respect of FIGS. 1 and 2. For example, every 25 hours (for example) the system makes a couple of adjustments and asks for the user's feedback as to whether these are better/worse than the current setting and based upon the user's responses a variation to the settings is established. It would also be evident that via one or more devices and/or systems and/or networks such as described supra in respect of FIGS. 1 and 2 the user may employ the methodologies according to embodiments of the invention within a variety of locations in conjunction with a single display or multiple displays. For example, a user may employ a virtual reality gaming headset at home and filtered glasses at work.

It would also be evident that the users may interact periodically with eye tests, eye charts, etc. for progress monitoring wherein these may be administered remotely or within the controlled environments. Within other embodiments of the invention a user may access a software download providing functionality to their electronic device to perform methodologies according to embodiments of the invention. Such downloads may for example be via software applications, social media feeds, etc. whilst user's employing the methodologies may similarly be members of social media and social media groups relating different medical conditions etc. whilst tracking their progress etc. within a private group providing support, feedback, encouragement etc.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may vary in implementation where the memory is employed in storing software codes for subsequent execution to that when the memory is employed in executing the software codes. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels and/or various other mediums capable of storing, containing or carrying instruction(s) and/or data.

The methodologies described herein are, in one or more embodiments, performable by a machine which includes one or more processors that accept code segments containing instructions. For any of the methods described herein, when the instructions are executed by the machine, the machine performs the method. Any machine capable of executing a set of instructions (sequential or otherwise) that specify actions to be taken by that machine are included. Thus, a typical machine may be exemplified by a typical processing system that includes one or more processors. Each processor may include one or more of a CPU, a graphics-processing unit, and a programmable DSP unit. The processing system further may include a memory subsystem including main RAM and/or a static RAM, and/or ROM. A bus subsystem may be included for communicating between the components. If the processing system requires a display, such a display may be included, e.g., a liquid crystal display (LCD). If manual data entry is required, the processing system also includes an input device such as one or more of an alphanumeric input unit such as a keyboard, a pointing control device such as a mouse, and so forth.

The memory includes machine-readable code segments (e.g. software or software code) including instructions for performing, when executed by the processing system, one of more of the methods described herein. The software may reside entirely in the memory, or may also reside, completely or at least partially, within the RAM and/or within the processor during execution thereof by the computer system. Thus, the memory and the processor also constitute a system comprising machine-readable code.

In alternative embodiments, the machine operates as a standalone device or may be connected, e.g., networked to other machines, in a networked deployment, the machine may operate in the capacity of a server or a client machine in server-client network environment, or as a peer machine in a peer-to-peer or distributed network environment. The machine may be, for example, a computer, a server, a cluster of servers, a cluster of computers, a web appliance, a distributed computing environment, a cloud computing environment, or any machine capable of executing a set of instructions (sequential or otherwise) that specify actions to be taken by that machine. The term "machine" may also be taken to include any collection of machines that individually or jointly execute a set (or multiple sets) of instructions to perform any one or more of the methodologies discussed herein.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for reducing binocular dysfunction in amblyopia, the method comprising:
establishing a first image for presentation to a left eye of a user and a second image for presentation to a right eye of the user, each of the first image and the second image generated by modification of a source image in dependence upon a characteristic of at least one of a neural condition and a neurological condition of the user;
wherein the modification is such that the left eye and the right eye of the user each see scattered segments of the source image and areas between the scattered segments are masked, neither the user's left eye nor right eye receiving a complete representation of the source image, wherein transitions between the scattered segments and the masked areas are gradual, and wherein the modification of the source image is related to at least one of the following forms of information content: intensity, contrast, mean luminance, temporal frequency, spatial frequency, depth, motion, and orientation, such that one of the first image and the second image received by a fixing eye contains less information content than the other of the first image and the second image.

2. The method according to claim 1, wherein
the source image is an item of source image which is processed to generate the first image and the second image for display to the user; or
the source image is the user's field of view and the first image and the second image are generated by establishing a first mask within a left optical system through which the user views the world with their left eye and a second mask with a right optical system through which the user views the world with their right eye.

3. The method according to claim 1, wherein
the modification to the source image comprises applying a first mask to the left eye and a second mask to the right eye, wherein
the second mask is the inverse of the first mask and each of the first mask and the second mask and transitions from masked regions to unmasked regions are gradual.

4. The method according to claim 1, wherein
the modification to the source image comprises applying a first mask to the left eye and a second mask to the right eye, wherein
a first predetermined portion of the source image is presented to the user via the first mask;
a second predetermined portion of the source image is presented to the user via the second mask; and
a third predetermined portion of the source image is presented to the user via both the first mask and the second mask.

5. The method according to claim 1, wherein
the images presented to the left and right eyes are either:
presented on different displays;
presented on different regions of a single display; and
presented overlaid on a single display wherein an appropriate filtering of the single display is performed via first and second filters disposed in front of the user's eyes.

6. The method according to claim 5, wherein
the first and second filters are at least one of polarization filters and wavelength filters.

7. The method according to claim 1, wherein
the first mask and the second mask are either complementary dichoptic random spatial masks or dichoptic random spatial masks.

8. The method according to claim 1, wherein
the first mask and the second mask are static or at least one of dynamic in location and dynamic in a mask property.

9. A system for reducing binocular dysfunction in amblyopia, the system comprising:
a module comprising:
a first port for receiving first electronic content for display to a user;
a second port for providing second electronic content to a display device associated with the user; and
a processing circuit configured for modifying, according to a characteristic of a neurological condition of the user, the first electronic content to generate the second electronic content;
wherein the modification is such that a left eye and right eye of the user receive different images based on the first and second electronic content and such that the left eye and the right eye of the user each see scattered segments of one image and areas between the scattered segments are masked, neither the user's left eye nor right eye receiving a complete representation of the electronic content,
wherein transitions between the scattered segments and the masked areas are gradual, and
wherein the modification is related to at least one of the following forms of information content: intensity, contrast, mean luminance, temporal frequency, spatial frequency, depth, motion, and orientation, such that one of the images is received by a fixing eye and contains less information content than the other image.

10. The system according to claim 9, wherein
the modification to the electronic content comprises applying a first mask to the left eye and a second mask to the right eye, wherein
the second mask is the inverse of the first mask and each of the first mask and the second mask and transitions from masked regions to unmasked regions are gradual.

11. The system according to claim 9, wherein
the modification to the electronic content comprises applying a first mask to the left eye and a second mask to the right eye, wherein
a first predetermined portion of the electronic content is presented to the user via the first mask;
a second predetermined portion of the electronic content is presented to the user via the second mask; and
a third predetermined portion of the electronic content is presented to the user via both the first mask and the second mask.

12. The system according to claim 9, wherein
the images presented to the left and right eyes are either:
presented on different display devices;
presented on different regions of a single display device; and
presented overlaid on a single display wherein an appropriate filtering of the single display device is performed via first and second filters disposed in front of the user's eyes.

13. The system according to claim 12, wherein
the first and second filters are at least one of polarization filters and wavelength filters.

14. The system according to claim 9, wherein the first mask and the second mask are either complementary dichoptic random spatial masks or dichoptic random spatial masks.

15. The system according to claim 9, wherein the first mask and the second mask are static or at least one of dynamic in location and dynamic in a mask property.

16. The system according to claim 9, wherein the processing circuit forms part of an electronic device selected from group comprising a portable electronic device, a television, a set-top box, a three-dimensional (3D) television, a smartphone, a laptop computer, a tablet computer, a gaming console, and a media player.

17. The system according to claim 9, wherein the processing circuit is an original part of an electronic device and is modified by at least one of a software revision, a firmware revision, and a software application.

18. A non-volatile, non-transitory storage medium storing executable instructions for execution by a processor which when executed result in a process for reducing binocular dysfunction in amblyopia being performed, the process comprising:

establishing a first image for presentation to a left eye of a user and a second image for presentation to a right eye of the user, each of the first image and the second image generated by modification of a source image in dependence upon a characteristic of an optical condition of the user;

wherein the modification is such that the left eye and the right eye of the user each see scattered segments of the source image and areas between the scattered segments are masked, neither the user's left eye nor right eye receiving a complete representation of the source image, wherein transitions between the scattered segments and the masked areas are gradual, and wherein the modification of the source image is related to at least one of the following forms of information content: intensity, contrast, mean luminance, temporal frequency, spatial frequency, depth, motion, and orientation, such that one of the first image and the second image received by a fixing eye contains less information content than the other of the first image and the second image.

* * * * *